United States Patent
Sharma et al.

(10) Patent No.: US 9,132,092 B1
(45) Date of Patent: Sep. 15, 2015

(54) PHARMACEUTICAL COMPOSITION OF DOXYCYCLINE

(71) Applicant: RANBAXY LABORATORIES LIMITED, New Delhi, Delhi (IN)

(72) Inventors: Ravish Kumar Sharma, Khargone (IN); Pulak Kumar Metia, Howrah (IN); Ravinder Singh, Gurgaon (IN); Rajesh Srikrishan Shear, Gurgaon (IN); Anuj Kumar Fanda, Ghaziabad (IN); Satish Kumar Jain, Bilaspur (IN); Romi Barat Singh, Varanasi (IN); Swarna Pappu, Monroe, NJ (US); Prabhakar Konatham, Monmouth Junction, NJ (US); Pruthvipathy Katikaneni, Parsippany, NJ (US)

(73) Assignee: RANBAXY LABORATORIES LIMITED, New Delhi (IN)

( * ) Notice: Subject to any disclaimer, the term of this patent is extended or adjusted under 35 U.S.C. 154(b) by 0 days.

(21) Appl. No.: 14/326,949

(22) Filed: Jul. 9, 2014

(51) Int. Cl.
*A61K 31/65* (2006.01)
*A61K 9/52* (2006.01)
*A61K 9/20* (2006.01)
*A61K 9/24* (2006.01)

(52) U.S. Cl.
CPC .............. *A61K 9/2054* (2013.01); *A61K 9/2009* (2013.01); *A61K 9/209* (2013.01); *A61K 9/2013* (2013.01); *A61K 9/2027* (2013.01); *A61K 31/65* (2013.01)

(58) Field of Classification Search
CPC ............................. A61K 31/65; A61K 9/2027
USPC .......................................... 514/152; 424/457
See application file for complete search history.

(56) References Cited

U.S. PATENT DOCUMENTS 7,749,532 B2    7/2010    Chang et al. .................. 424/458

*Primary Examiner* — Raymond Henley, III

(57) ABSTRACT

The present invention relates to a pharmaceutical composition comprising (i) 50% to 99% of doxycycline as an immediate-release portion; (ii) 1% to 50% of doxycycline as a controlled-release portion; and (iii) one or more pharmaceutically acceptable excipients; wherein the pharmaceutical composition provides a total daily dosage of 40 mg when administered once daily. It also relates to process for preparation of the pharmaceutical composition and its use for treating rosacea.

12 Claims, No Drawings

PHARMACEUTICAL COMPOSITION OF DOXYCYCLINE

FIELD OF THE INVENTION

The present invention relates to a pharmaceutical composition comprising (i) 50% to 99% of doxycycline and one or more pharmaceutically acceptable excipients as an immediate-release portion; and (ii) 1% to 50% of doxycycline, a controlled-release polymer, and one or more pharmaceutically acceptable excipients as a controlled-release portion, wherein the pharmaceutical composition provides a total daily dosage of 40 mg when administered once daily. Further, it relates to a process for the preparation of said pharmaceutical composition and its use for treating rosacea.

BACKGROUND OF THE INVENTION

U.S. Pat. No. 7,749,532 discloses the use of doxycycline at sub-antimicrobial doses to treat rosacea. It further discloses a doxycycline composition consisting of (i) an immediate-release portion consisting of about 30 mg doxycycline, and (ii) a delayed-release portion consisting of about 10 mg doxycycline, in which the delayed-release portion is in the form of pellets coated with at least one enteric polymer. It further discloses that the enteric coating is such that there is no substantial release of doxycycline in the acidic stomach environment, and doxycycline is released only in the small intestine.

There remains a need in the art for a pharmaceutical composition of doxycycline which releases the drug in a continuous manner independent of the pH of the gastrointestinal tract. This is achieved by the pharmaceutical composition of the present invention which comprises specific amounts of doxycycline as immediate-release and controlled-release portions, in order to demonstrate a continuous release profile.

SUMMARY OF THE INVENTION

The present invention provides a pharmaceutical composition comprising (i) 50% to 99% of doxycycline and one or more pharmaceutically acceptable excipients as an immediate-release portion; and (ii) 1% to 50% of doxycycline, a controlled-release polymer, and one or more pharmaceutically acceptable excipients as a controlled-release portion, wherein the pharmaceutical composition provides a total daily dosage of 40 mg when administered once daily. It also provides a process for the preparation of the pharmaceutical composition and its use for the treatment of rosacea.

DETAILED DESCRIPTION OF THE INVENTION

Various embodiments and variants of the present invention are described hereinafter.

A first aspect of the present invention provides a pharmaceutical composition comprising (i) 50% to 99% of doxycycline and one or more pharmaceutically acceptable excipients as an immediate-release portion; and (ii) 1% to 50% of doxycycline, a controlled-release polymer, and one or more pharmaceutically acceptable excipients as a controlled-release portion, wherein the pharmaceutical composition provides a total daily dosage of 40 mg when administered once daily.

According to one embodiment of the above aspect, the immediate-release portion contains 75% of doxycycline and the controlled-release portion contains 25% of doxycycline.

According to another embodiment of the above aspect, the immediate-release portion contains 30 mg of doxycycline and the controlled-release portion contains 10 mg of doxycycline.

According to another embodiment of the above aspect, the immediate-release portion contains 65% of doxycycline and the controlled-release portion contains 35% of doxycycline.

According to another embodiment of the above aspect, the immediate-release portion contains 26 mg of doxycycline and the controlled-release portion contains 14 mg of doxycycline.

According to another embodiment of the above aspect, the immediate-release portion contains 60% of doxycycline and the controlled-release portion contains 40% of doxycycline.

According to another embodiment of the above aspect, the immediate-release portion contains 24 mg of doxycycline and the controlled-release portion contains 16 mg of doxycycline.

According to another embodiment of the above aspect, the controlled-release polymer is a cellulose polymer.

According to another embodiment of the above aspect, the one or more pharmaceutically acceptable excipients are selected from the group comprising binders, diluents, disintegrants, lubricants/glidants/antiadherants, plasticizers, or mixtures thereof.

According to yet another embodiment of the above aspect, the pharmaceutical composition is in the form of a tablet.

A second aspect of the present invention provides a process for the preparation of a pharmaceutical composition comprising (i) 50% to 99% of doxycycline and one or more pharmaceutically acceptable excipients as an immediate-release portion; and (ii) 1% to 50% of doxycycline, a controlled-release polymer, and one or more pharmaceutically acceptable excipients as a controlled-release portion, wherein the pharmaceutical composition provides a total daily dosage of 40 mg when administered once daily, and wherein the process comprises:
  a) preparing the immediate-release portion comprising doxycycline and one or more pharmaceutically acceptable excipients;
  b) preparing the controlled-release portion comprising doxycycline, a controlled-release polymer, and one or more pharmaceutically acceptable excipients; and
  c) processing the immediate-release portion and the controlled-release portion to form the pharmaceutical composition.

According to one embodiment of the above aspect, the pharmaceutical composition is a tablet prepared by combining the immediate-release portion and the controlled-release portion.

A third aspect of the present invention provides a method of treating rosacea by administering to a patient in need thereof a pharmaceutical composition comprising (i) 50% to 99% of doxycycline and one or more pharmaceutically acceptable excipients as an immediate-release portion; and (ii) 1% to 50% of doxycycline, a controlled-release polymer, and one or more pharmaceutically acceptable excipients as a controlled-release portion, wherein the pharmaceutical composition provides a total daily dosage of 40 mg when administered once daily.

The term "doxycycline", as used herein, refers to doxycycline and pharmaceutically acceptable salts thereof, including hydrates and solvates thereof, and crystalline or amorphous forms thereof. The preferred forms are the monohydrate form and the hyclate form.

The term "immediate-release portion", as used herein, refers to that portion of the dosage form which releases the drug immediately upon contact with gastric juices.

The term "controlled-release portion", as used herein, refers to that portion of the dosage form which releases the drug in a controlled manner over a period of time. Controlled-release can also be referred to as sustained-release (SR), prolonged-release (PR), or extended-release (ER). Suitable controlled-release polymers are selected from the group comprising hydroxypropylmethyl cellulose, microcrystalline cellulose, hydroxypropyl cellulose, methyl cellulose, sodium carboxymethyl cellulose, hydroxyethyl cellulose, carboxymethyl ethyl cellulose, ethyl cellulose, cellulose acetate, cellulose nitrate, other cellulose derivatives, polymethacrylic copolymer, poloxamers, polyoxyethylene stearate, polyvinylpyrrolidone, polyvinylpyrrolidone-polyvinylacetate copolymer, polyvinyl alcohol, polyethylene oxide, gums (e.g., xanthan gum, tragacanth gum, gum karaya, guar gum, acacia gum, and locust bean gum), a fatty acid, a fatty acid ester, an alkyl alcohol, wax, shellac, or mixtures thereof.

The term "pharmaceutically acceptable excipients", as used herein, includes any physiologically inert additives that are routinely used in pharmaceutical dosage forms. Pharmaceutically acceptable excipients may include, but are not limited to, binders, diluents, disintegrants, lubricants/glidants/antiadherants, plasticizers, or mixtures thereof.

Suitable binders are selected from the group comprising povidone, copovidone, hydroxypropylmethyl cellulose, hydroxypropyl cellulose, hydroxyethyl cellulose, methyl cellulose, ethyl cellulose, xanthan gum, gum acacia, gum arabic, tragacanth, sorbitol, dextrose, sucrose, mannitol, gelatin, pullulan, sodium alginate, propylene glycol, polyvinyl alcohol, corn syrup, methacrylates, carboxyvinyl polymers like carbomers, or mixtures thereof.

Suitable diluents are selected from the group comprising microcrystalline cellulose, powdered cellulose, dibasic calcium phosphate, tribasic calcium phosphate, calcium sulfate, calcium carbonate, lactose monohydrate, lactose anhydrous, sucrose, sorbitol, xylitol, erythritol, kaolin, calcium silicate, maltodextrin, starch, modified starch, e.g., pregelatinized starch, maize starch, corn starch, or mixtures thereof.

Suitable disintegrants are selected from the group comprising hydroxypropyl cellulose (L-HPC), crospovidone, croscarmellose sodium, carboxymethyl cellulose sodium, carboxymethyl cellulose calcium, sodium starch glycolate, gums, alginic acid or alginates, starch, corn starch, modified starch, carboxymethyl starch, polyacrylates, or mixtures thereof.

Suitable lubricants/glidants/antiadherents are selected from the group comprising magnesium stearate, hydrogenated vegetable oil, glyceryl behenate, glyceryl monostearate, stearic acid, sodium stearyl fumarate, sodium starch fumarate, calcium stearate, zinc stearate, aluminum silicate, talc, colloidal silicon dioxide, sucrose esters of fatty acid, waxes, silica gel, or mixtures thereof.

Suitable plasticizers are selected from the group comprising triethyl citrate, dibutyl sebacate, acetylated triacetin, tributyl citrate, glyceryl tributyrate, monoglyceride, rapeseed oil, olive oil, sesame oil, acetyl tributyl citrate, acetyl triethyl citrate, glycerin, sorbitol, diethyl oxalate, diethyl phthalate, diethyl malate, diethyl fumarate, dibutyl succinate, diethyl malonate, dioctyl phthalate, or mixtures thereof.

The pharmaceutical composition of the present invention may further comprise opacifiers selected from the group comprising titanium dioxide, manganese dioxide, iron oxide, silicon dioxide, or mixtures thereof.

Coloring agents include any FDA approved color for oral use.

Various solvents that may be employed during the preparation of the pharmaceutical composition of the present invention are selected from the group comprising methyl alcohol, ethyl alcohol, isopropyl alcohol, n-butyl alcohol, acetone, acetonitrile, chloroform, methylene chloride, water, or mixtures thereof.

The immediate-release portion and the controlled-release portion may be in the form of pellets, beads, beadlets, granules, spheres or spheroids, minitablets, particles, or powders. The immediate-release portion and the controlled-release portion may be prepared by wet granulation, dry granulation, direct compression, drug layering over an inert core, or extrusion spheronization. The inert core may be in the form of sugar spheres, non-pareil seeds, or Celpheres®.

The pharmaceutical composition is in the form of tablet or capsule. The tablet may be a single layered, bilayered, or an inlay tablet. The tablet may be further coated with a film coating prepared by using a film-forming polymer and one or more pharmaceutically acceptable excipients.

Suitable film-forming polymers are selected from hydroxypropylmethyl cellulose, ethyl cellulose, methyl cellulose, hydroxyethyl cellulose, hydroxypropyl cellulose, sodium carboxymethyl cellulose, cellulose acetate, hydroxypropylmethyl cellulose phthalate, cellulose acetate trimellitate, methacrylic acid copolymers, e.g., Eudragit®, polyvinylpyrrolidone, polyvinyl alcohol, polyethylene glycol, or mixtures thereof. A preferred film-forming polymer is hydroxypropylmethyl cellulose. Other suitable film-forming polymers which are known in the art, such as Opadry®, may also be used.

The invention is further illustrated by the following examples, which are for illustrative purposes only and should not be construed as limiting the scope of the invention in any way.

EXAMPLES

| Ingredients | Percent (%) w/w |
|---|---|
| Immediate-Release Portion | |
| Doxycycline hyclate equivalent to doxycycline base 30 mg | 11.20 |
| Microcrystalline cellulose | 32.49 |
| Crospovidone | 2.43 |
| Polyvinyl pyrrolidone | 1.70 |
| Magnesium stearate | 0.49 |
| Colloidal silicon dioxide | 0.24 |
| Controlled-Release Portion | |
| Doxycycline hyclate equivalent to doxycycline base 10 mg | 3.73 |
| Microcrystalline cellulose | 29.76 |
| Hydroxypropylmethyl cellulose (Methocel ® K100 LVCR) | 7.28 |
| Hydroxypropylmethyl cellulose (Methocel ® K4M CR) | 7.28 |
| Magnesium stearate | 0.49 |
| Film Coating | |
| Opadry ® | 2.91 |
| Purified water | q.s. |

Procedure:
Immediate-Release Portion
1. Doxycycline hyclate, microcrystalline cellulose, crospovidone and polyvinyl pyrrolidone are blended.
2. The blend obtained in step 1 is mixed with magnesium stearate and colloidal silicon dioxide to obtain the final blend.

Controlled-Release Portion
  3. Doxycycline hyclate, microcrystalline cellulose and hydroxypropylmethyl cellulose polymers are blended.
  4. Magnesium stearate is added to the blend of step 3 to obtain the final blend.
Compression
  5. The blends obtained in step 2 and step 4 are compressed to form a bilayer tablet.
  6. The bilayer tablet obtained in step 5 is film coated using an Opadry® solution.

| Ingredients | Percent (%) w/w |
|---|---|
| Immediate-Release Portion | |
| Doxycycline hyclate equivalent to doxycycline base 30 mg | 11.20 |
| Microcrystalline cellulose | 32.49 |
| Crospovidone | 2.43 |
| Polyvinyl pyrrolidone | 1.70 |
| Magnesium stearate | 0.49 |
| Colloidal silicon dioxide | 0.24 |
| Controlled-Release Portion | |
| Doxycycline hyclate equivalent to doxycycline base 10 mg | 3.73 |
| Polyvinyl pyrrolidone | 1.46 |
| Microcrystalline cellulose | 28.31 |
| Hydroxypropylmethyl cellulose (Methocel ® K100 LVCR) | 7.28 |
| Hydroxypropylmethyl cellulose (Methocel ® K4M CR) | 7.28 |
| Purified water | q.s. |
| Magnesium stearate | 0.48 |
| Film Coating | |
| Opadry ® | 2.91 |
| Purified water | q.s. |

Procedure:
Immediate-Release Portion
  1. Doxycycline hyclate, microcrystalline cellulose, crospovidone, and polyvinyl pyrrolidone are blended.
  2. The blend obtained in step 1 is mixed with magnesium stearate and colloidal silicon dioxide to obtain the final blend.
Controlled-Release Portion
  3. Polyvinyl pyrrolidone is dissolved in purified water to form a binder solution.
  4. Doxycycline hyclate is added to the binder solution obtained in step 3 to form a drug-binder solution.
  5. Microcrystalline cellulose and hydroxypropylmethyl cellulose are loaded into a top spray granulation assembly and are granulated using the drug-binder solution of step 4 to obtain granules.
  6. The granules obtained in step 5 are lubricated with magnesium stearate.
Compression
  7. The blend obtained in step 2 and the lubricated granules obtained in step 6 are compressed to form a bilayer tablet.
  8. The bilayer tablet obtained in step 7 is film coated using an Opadry® solution.

| Ingredients | Percent (%) w/w |
|---|---|
| Drug Layering | |
| Non pareil seeds | 26.25 |
| Doxycycline hyclate equivalent to doxycycline base 10 mg | 3.03 |
| Hydroxypropylmethyl cellulose | 0.63 |
| Purified water | q.s. |
| Controlled-Release Portion | |
| Ethyl cellulose | 3.56 |
| Dibutyl sebacate | 0.37 |
| Hydroxypropylmethyl cellulose | 0.19 |
| Isopropyl alcohol | q.s. |
| Purified water | q.s. |
| Colloidal silicon dioxide | 0.37 |
| Immediate-Release Portion | |
| Doxycycline hyclate equivalent to doxycycline base 30 mg | 9.38 |
| Microcrystalline cellulose | 53.00 |
| Crospovidone | 1.97 |
| Polyvinyl pyrrolidone | 0.66 |
| Magnesium stearate | 0.39 |
| Colloidal silicon dioxide | 0.20 |

Procedure:
Drug Layering
  1. Hydroxypropylmethyl cellulose is dissolved in purified water to form a binder solution.
  2. Doxycycline hyclate is added to the binder solution of step 1 to form a drug-binder solution.
  3. Sugar spheres are coated using the drug-binder solution obtained in step 2 to obtain drug layered sugar spheres.
  4. The drug layered sugar spheres obtained in step 3 are dried.
Controlled-Release Portion
  5. Isopropyl alcohol and purified water are mixed and dibutyl sebacate is added to the mixture, followed by the addition of ethyl cellulose and hydroxypropylmethyl cellulose with continuous stirring to form a clear solution.
  6. Colloidal silicon dioxide is dispersed in the clear solution obtained in step 5 to form a coating solution.
  7. The drug layered dried sugar spheres obtained in step 4 are coated with the coating solution obtained in step 6 to obtain coated pellets.
Immediate-Release Portion
  8. Doxycycline hyclate, microcrystalline cellulose, crospovidone, and polyvinyl pyrrolidone are blended.
  9. The blend obtained in step 8 is mixed with magnesium stearate and colloidal silicon dioxide to obtain the final blend.
Compression
  10. The coated pellets obtained in step 7 and the final blend obtained in step 9 are compressed to form a tablet.

| Ingredients | Percent (%) w/w |
|---|---|
| Drug Layering | |
| Non pareil seeds | 28.74 |
| Doxycycline hyclate equivalent to doxycycline base 10 mg | 3.32 |
| Hydroxypropylmethyl cellulose | 0.68 |
| Purified water | q.s. |
| Controlled-Release Portion | |
| Ethyl cellulose | 3.90 |
| Dibutyl sebacate | 0.41 |
| Hydroxypropylmethyl cellulose | 0.21 |
| Isopropyl alcohol | q.s. |
| Purified water | q.s. |
| Colloidal silicon dioxide | 0.41 |

| Ingredients | Percent (%) w/w |
|---|---|
| Immediate-Release Portion | |
| Doxycycline hyclate equivalent to doxycycline base 30 mg | 10.27 |
| Hydroxypropylmethyl cellulose | 2.05 |
| Purified water | q.s. |
| Compression Blend | |
| Microcrystalline cellulose | 43.11 |
| Crospovidone | 4.31 |
| Hydroxypropyl cellulose | 2.01 |
| Magnesium stearate | 0.58 |

Procedure:
Drug Layering
 1. Hydroxypropylmethyl cellulose is dissolved in purified water to form a binder solution.
 2. Doxycycline hyclate is added to the binder solution of step 1 to form a drug-binder solution.
 3. Sugar spheres are coated using the drug-binder solution of step 2 to obtain drug layered sugar spheres.
 4. The drug layered sugar spheres obtained in step 3 are dried.
Controlled-Release Portion
 5. Isopropyl alcohol and purified water are mixed and dibutyl sebacate is added to the mixture, followed by the addition of ethyl cellulose and hydroxypropylmethyl cellulose under continuous stirring to form a clear solution.
 6. Colloidal silicon dioxide is then dispersed in the clear solution obtained in step 5 to form a coating solution.
 7. The drug layered dried sugar spheres obtained in step 4 are coated with the coating solution obtained in step 6 to obtain coated pellets.
Immediate-Release Portion
 8. Hydroxypropylmethyl cellulose is dissolved in purified water and doxycycline hyclate is added to obtain a drug-binder solution.
 9. The drug-binder solution obtained in step 8 is coated onto the coated pellets obtained in step 7.
Compression
 10. Microcrystalline cellulose, crospovidone, and hydroxypropyl cellulose are blended.
 11. The blend obtained in step 10 is lubricated with magnesium stearate.
 12. The coated pellets obtained in step 9 and the lubricated blend obtained in step 11 are compressed to form a tablet.

| Ingredients | Percent (%) w/w |
|---|---|
| Immediate-Release Portion | |
| Doxycycline hyclate equivalent to doxycycline base 30 mg | 11.99 |
| Microcrystalline cellulose (Avicel ® PH-102) | 31.07 |
| Crospovidone | 2.91 |
| Polyvinyl pyrrolidone | 1.70 |
| Colloidal silicon dioxide | 0.24 |
| Iron oxide yellow | 0.10 |
| Magnesium stearate | 0.49 |
| Controlled-Release Portion | |
| Doxycycline hyclate equivalent to doxycycline base 10 mg | 3.99 |
| Microcrystalline cellulose (Avicel ® PH-102) | 13.91 |
| Microcrystalline cellulose (Avicel ® PH-200) | 13.86 |
| Hydroxypropylmethyl cellulose (Methocel ® K100 LVCR) | 7.28 |
| Hydroxypropylmethyl cellulose (Methocel ® K4M CR) | 7.28 |
| Polyvinyl pyrrolidone | 1.46 |
| Colloidal silicon dioxide | 0.24 |
| Magnesium stearate | 0.48 |
| Coating | |
| Opadry ® | 3.00 |

Procedure:
Immediate-Release Portion
 1. Doxycycline hyclate, microcrystalline cellulose, crospovidone, polyvinyl pyrrolidone, colloidal silicon dioxide, magnesium stearate, and iron oxide yellow were mixed to form a blend.
Controlled-Release Portion
 2. Doxycycline hyclate, microcrystalline cellulose, hydroxypropylmethyl cellulose, polyvinyl pyrrolidone, colloidal silicon dioxide, and magnesium stearate were mixed to form a blend.
Compression
 3. The blend obtained in step 2 was compressed followed by the compression of the blend obtained in step 1 to form a bilayer tablet.
 4. The bilayer tablet obtained in step 3 was further film coated using Opadry®.

| Ingredients | Percent (%) w/w |
|---|---|
| Immediate-Release Portion | |
| Doxycycline monohydrate | 12.01 |
| Microcrystalline cellulose (Avicel ® PH-102) | 32.96 |
| Crospovidone | 4.31 |
| Colloidal silicon dioxide | 0.38 |
| Magnesium stearate | 0.35 |
| Controlled-Release Portion | |
| Doxycycline monohydrate | 4.00 |
| Microcrystalline cellulose (Avicel ® PH-102) | 14.51 |
| Lactose monohydrate | 14.52 |
| Hydroxypropylmethyl cellulose (Methocel ® K100 LVCR) | 8.08 |
| Hydroxypropylmethyl cellulose (Methocel ® K4M CR) | 8.08 |
| Colloidal silicon dioxide | 0.43 |
| Magnesium stearate | 0.38 |

Procedure:
Immediate-Release Portion
 1. Doxycycline monohydrate, microcrystalline cellulose, and colloidal silicon dioxide were mixed to form a blend.
 2. Crospovidone was added to the blend obtained in step 1.
 3. The blend obtained in step 2 was lubricated with magnesium stearate to form the final blend.
Controlled-Release Portion
 4. Doxycycline monohydrate, microcrystalline cellulose, and colloidal silicon dioxide were mixed to form a blend.
 5. Lactose monohydrate and hydroxypropylmethyl cellulose were added to the blend of step 4 and mixed to obtain a blend.
 6. The blend obtained in step 5 was lubricated with magnesium stearate to form the final blend.

Compression
7. The final blend obtained in step 3 was compressed followed by the compression of the final blend obtained in step 6 to form a bilayer tablet.

| Ingredients | Percent (%) w/w |
|---|---|
| Immediate-Release Portion | |
| Doxycycline monohydrate | 12.01 |
| Microcrystalline cellulose (Avicel ® PH-102) | 32.96 |
| Crospovidone | 4.31 |
| Colloidal silicon dioxide | 0.38 |
| Magnesium stearate | 0.35 |
| Controlled-Release Portion | |
| Doxycycline monohydrate | 4.00 |
| Microcrystalline cellulose (Avicel ® PH-102) | 14.51 |
| Lactose monohydrate | 14.52 |
| Hydroxypropylmethyl cellulose (Methocel ® K4 MCR) | 16.15 |
| Colloidal silicon dioxide | 0.43 |
| Magnesium stearate | 0.38 |

Procedure:
Immediate-Release Portion
1. Doxycycline monohydrate, microcrystalline cellulose, and colloidal silicon dioxide were mixed to form a blend.
2. Crospovidone was added to the blend obtained in step 1.
3. The blend obtained in step 2 was lubricated with magnesium stearate to form the final blend.

Controlled-Release Portion
4. Doxycycline monohydrate, microcrystalline cellulose, and colloidal silicon dioxide were mixed to form a blend.
5. Lactose monohydrate and hydroxypropylmethyl cellulose were added to the blend of step 4 and mixed to obtain a blend.
6. The blend obtained in step 5 was lubricated with magnesium stearate to form the final blend.

Compression
7. The final blend obtained in step 3 was compressed followed by the compression of the final blend obtained in step 6 to form a bilayer tablet.

| Ingredients | Percent (%) w/w |
|---|---|
| Immediate-Release Portion | |
| Doxycycline monohydrate | 10.41 |
| Microcrystalline cellulose (Avicel ® PH-102) | 34.56 |
| Crospovidone | 4.31 |
| Colloidal silicon dioxide | 0.38 |
| Magnesium stearate | 0.35 |
| Controlled-Release Portion | |
| Doxycycline monohydrate | 5.60 |
| Microcrystalline cellulose (Avicel ® PH-102) | 14.06 |
| Lactose monohydrate | 14.13 |
| Hydroxypropylmethyl cellulose (Methocel ® K100 LVCR) | 7.69 |
| Hydroxypropylmethyl cellulose (Methocel ® K4 MCR) | 7.69 |
| Colloidal silicon dioxide | 0.43 |
| Magnesium stearate | 0.38 |

Procedure:
Immediate-Release Portion
1. Doxycycline monohydrate, microcrystalline cellulose, and colloidal silicon dioxide were mixed to form a blend.
2. Crospovidone was added to the blend obtained in step 1.
3. The blend obtained in step 2 was lubricated with magnesium stearate to form the final blend.

Controlled-Release Portion
4. Doxycycline monohydrate, microcrystalline cellulose, and colloidal silicon dioxide were mixed to form a blend.
5. Lactose monohydrate and hydroxypropylmethyl cellulose were added to the blend of step 4 and mixed to obtain a blend.
6. The blend obtained in step 5 was lubricated with magnesium stearate to form the final blend.

Compression
7. The final blend obtained in step 3 was compressed followed by the compression of the final blend obtained in step 6 to form a bilayer tablet.

| Ingredients | Percent (%) w/w |
|---|---|
| Immediate-Release Portion | |
| Doxycycline monohydrate | 10.40 |
| Microcrystalline cellulose (Avicel ® PH-102) | 34.50 |
| Crospovidone | 4.30 |
| Colloidal silicon dioxide | 0.40 |
| Magnesium stearate | 0.40 |
| Iron oxide yellow | 0.10 |
| Controlled-Release Portion | |
| Doxycycline monohydrate | 5.60 |
| Microcrystalline cellulose (Avicel ® PH-102) | 14.40 |
| Lactose monohydrate | 13.80 |
| Hydroxypropylmethyl cellulose (Methocel ® K4M CR) | 15.40 |
| Colloidal silicon dioxide | 0.40 |
| Magnesium stearate | 0.40 |
| Coating | |
| Opadry ® | 3.00 |

Procedure:
Immediate-Release Portion
1. Doxycycline monohydrate, microcrystalline cellulose, iron oxide yellow, colloidal silicon dioxide, crospovidone, and magnesium stearate were mixed to form a blend.

Controlled-Release Portion
2. Doxycycline monohydrate, microcrystalline cellulose, and colloidal silicon dioxide were mixed to form a blend.
3. Lactose monohydrate and hydroxypropylmethyl cellulose were added to the blend of step 2 and mixed to obtain a blend.
4. The blend obtained in step 3 was lubricated with magnesium stearate to form the final blend.

Compression
5. The blend obtained in step 1 was compressed followed by the compression of the final blend obtained in step 4 to form a bilayer tablet.
6. The tablet obtained in step 5 was further film coated using Opadry®.

| Ingredients | Percent (%) w/w |
|---|---|
| Immediate-Release Portion | |
| Doxycycline monohydrate | 9.61 |
| Microcrystalline cellulose (Avicel ® PH-102) | 35.25 |

-continued

| Ingredients | Percent (%) w/w |
|---|---|
| Crospovidone | 4.31 |
| Colloidal silicon dioxide | 0.38 |
| Magnesium stearate | 0.35 |
| Iron oxide yellow | 0.11 |
| Controlled-Release Portion | |
| Doxycycline monohydrate | 6.40 |
| Microcrystalline cellulose (Avicel ®PH-102) | 12.84 |
| Lactose monohydrate | 13.78 |
| Hydroxypropylmethyl cellulose (Methocel ® K100 LVCR) | 8.08 |
| Hydroxypropylmethyl cellulose (Methocel ® K4M CR) | 8.08 |
| Colloidal silicon dioxide | 0.43 |
| Magnesium stearate | 0.38 |
| Coating | |
| Opadry ® | 2.99 |

Procedure:
Immediate-Release Portion
 1. Doxycycline monohydrate, microcrystalline cellulose, iron oxide yellow, crospovidone, colloidal silicon dioxide, and magnesium stearate were mixed to form a blend.
Controlled-Release Portion
 2. Doxycycline monohydrate, microcrystalline cellulose, and colloidal silicon dioxide were mixed to form a blend.
 3. Lactose monohydrate was added to the blend obtained in step 2, followed by the addition of hydroxypropylmethyl cellulose to obtain a blend.
 4. The blend obtained in step 3 was lubricated with magnesium stearate to form the final blend.
Compression
 5. The blend obtained in step 1 was compressed followed by the compression of the final blend obtained in step 4 to form a bilayer tablet.
 6. The tablet obtained in step 5 was further film coated using Opadry®.

Dissolution Data

The compositions prepared in Examples 5-10 were subjected to dissolution studies which involved carrying out the dissolution of the compositions at pH 1.2 for 2 hours in 750 mL of 0.1N HCl using dissolution apparatus (USP type II) with paddles rotating at 75 rpm. The samples were withdrawn at regular intervals. After 2 hours, the media was replaced with 950 mL of pH 6.0 buffer.

The dissolution profiles are provided in Table 1 below.

TABLE 1

| | % Doxycycline Dissolved | | | | |
|---|---|---|---|---|---|
| | Acid Stage (0.1N HCl, pH 1.2) 750 mL | | | | Buffer Stage (pH 6.0 buffer) 950 mL |
| Time (minutes)→ | 15 | 30 | 60 | 120 | 240 |
| Example 5 | 80 | 83 | 86 | 91 | 97 |
| Example 6 | 74 | 77 | 81 | 88 | 95 |
| Example 7 | 77 | 79 | 84 | 88 | 94 |
| Example 8 | 78 | 81 | 85 | 92 | 100 |
| Example 9 | 62 | 69 | 74 | 81 | 89 |
| Example 10 | 63 | 66 | 70 | 77 | 85 |

The controlled-release portion and immediate-release portion of Example 9 and Example 10 were separately subjected to dissolution conditions in 750 mL of 0.1N HCl at pH 1.2. The dissolution profile is provided in Table 2 below.

TABLE 2

| | | % Doxycycline Dissolved Acid Stage (0.1N HCl, pH 1.2) 750 mL | | | | |
|---|---|---|---|---|---|---|
| | Time (minutes) → | 15 | 30 | 60 | 120 | 240 |
| Example 9 | Controlled-Release Portion | 5 | 5 | 7 | 10 | 16 |
| | Immediate-Release Portion | 65 | 65 | 66 | 65 | 64 |
| Example 10 | Controlled-Release Portion | 3 | 5 | 7 | 10 | 16 |
| | Immediate-Release Portion | 59 | 60 | 60 | 60 | 61 |

| Ingredients | Percent (%) w/w |
|---|---|
| Immediate-Release Portion (Without Drug) | |
| Microcrystalline cellulose (Avicel ® PH-102) | 43.11 |
| Crospovidone | 2.91 |
| Polyvinyl pyrrolidone | 1.70 |
| Colloidal silicon dioxide | 0.24 |
| Iron oxide yellow | 0.10 |
| Magnesium stearate | 0.49 |
| Controlled-Release Portion | |
| Doxycycline hyclate equivalent to doxycycline base 10 mg | 3.99 |
| Microcrystalline cellulose (Avicel ® PH-102) | 13.91 |
| Microcrystalline cellulose (Avicel ® PH-200) | 13.86 |
| Hydroxypropylmethyl cellulose (Methocel ® K100 LVCR) | 7.28 |
| Hydroxypropylmethyl cellulose (Methocel ® K4M CR) | 7.28 |
| Polyvinyl pyrrolidone | 1.46 |
| Colloidal silicon dioxide | 0.24 |
| Magnesium stearate | 0.48 |
| Coating | |
| Opadry ® | 3.00 |

Procedure:
Immediate-Release Portion (Without Drug)
 1. Microcrystalline cellulose, crospovidone, and polyvinyl pyrrolidone were mixed to form a blend.
 2. Colloidal silicon dioxide and magnesium stearate were added to the blend obtained in step 1.
 3. Iron oxide yellow was added to the blend obtained in step 2 to form the final blend.
Controlled-Release Portion
 4. Doxycycline hyclate, microcrystalline cellulose, hydroxypropylmethyl cellulose, and polyvinyl pyrrolidone were mixed to form a blend.
 5. Colloidal silicon dioxide and magnesium stearate were added to the blend obtained in step 4 to form the final blend.
Compression
 6. The final blend obtained in step 5 was compressed followed by the compression of the final blend obtained in step 3 to form a bilayer tablet.
 7. The tablet obtained in step 6 was further film coated using Opadry®.
Dissolution Data The composition of Example 11 was subjected to a dissolution method which involves carrying out the dissolution of the composition in 900 mL of 0.1N HCl having pH of 1.2 using dissolution apparatus (USP type II) with paddles rotating at 75 rpm. The dissolution profile is provided in Table 3 below.

TABLE 3

Percent (%) Drug Dissolution
(0.1N HCl, 900 mL)

| Time (minutes) | Total Tablet (Example 5) | Example 11 Controlled-Release Portion | |
|---|---|---|---|
| | | As 10 mg claim of Controlled-Release | As 40 mg claim of Complete Tablet |
| 5 | 77 | 5 | 1 |
| 10 | 79 | 11 | 3 |
| 15 | 80 | 14 | 4 |
| 30 | 83 | 21 | 6 |
| 60 | 86 | 35 | 9 |
| 120 | 91 | 54 | 14 |
| 180 | 94 | 71 | 18 |
| 240 | 97 | 85 | 22 |

It is evident from the data provided in Table 3 that in the first 5 minutes to 15 minutes, there was 75% of drug release from the tablet.

| Ingredients | Percent (%) w/w |
|---|---|
| Immediate-Release Portion | |
| Doxycycline hyclate equivalent to doxycycline base 30 mg | 11.99 |
| Microcrystalline cellulose (Avicel ® PH-102) | 31.07 |
| Crospovidone | 2.91 |
| Polyvinyl pyrrolidone | 1.70 |
| Colloidal silicon dioxide | 0.24 |
| Iron oxide yellow | 0.10 |
| Magnesium stearate | 0.49 |
| Controlled-Release Portion (Without Drug) | |
| Microcrystalline cellulose (Avicel ® PH-102) | 17.90 |
| Microcrystalline cellulose (Avicel ® PH-200) | 13.86 |
| Hydroxypropylmethyl cellulose (Methocel ® K100 LVCR) | 7.28 |
| Hydroxypropylmethyl cellulose (Methocel ® K4M CR) | 7.28 |
| Polyvinyl pyrrolidone | 1.46 |
| Colloidal silicon dioxide | 0.24 |
| Magnesium stearate | 0.48 |
| Coating | |
| Opadry ® | 3.00 |

Procedure:
Immediate-Release Portion
1. Doxycycline hyclate, microcrystalline cellulose, crospovidone, and polyvinyl pyrrolidone were mixed to form a blend.
2. Colloidal silicon dioxide and magnesium stearate were added to the blend obtained in step 1.
3. Iron oxide yellow was added to the blend obtained in step 2 to form the final blend.

Controlled-Release Portion (Without Drug)
4. Microcrystalline cellulose, hydroxypropylmethyl cellulose, and polyvinyl pyrrolidone were mixed to form a blend.
5. Colloidal silicon dioxide and magnesium stearate were added to the blend obtained in step 4 to form the final blend.

Compression
6. The final blend obtained in step 5 was compressed followed by the compression of the final blend obtained in step 3 to form a bilayer tablet.
7. The tablet obtained in step 6 was further film coated using Opadry®.

Dissolution Data

The composition of Example 12 was subjected to a dissolution method which involves carrying out the dissolution of the composition in 900 mL of 0.1N HCl having pH of 1.2 using dissolution apparatus (USP type II) with paddles rotating at 75 rpm. The dissolution profile is provided in Table 4 below.

TABLE 4

| Time (minutes) | Percent (%) Drug Dissolution (0.1N HCl, 900 mL) Immediate-Release Portion as 30 mg claim for IR Layer |
|---|---|
| 5 | 101 |
| 10 | 102 |
| 15 | 102 |
| 30 | 101 |

It is evident from the data provided in Table 4 that in the first 5 minutes there was 100% drug release.

We claim:

1. A pharmaceutical composition comprising (i) 50-99% of doxycycline and one or more pharmaceutically acceptable excipients as an immediate-release portion; and (ii) 1-50% of doxycycline, a controlled-release polymer, and one or more pharmaceutically acceptable excipients as a controlled-release portion, wherein the pharmaceutical composition provides a total daily dosage of 40 mg when administered once daily.

2. The pharmaceutical composition according to claim 1, wherein the immediate-release portion contains 75% of doxycycline and the controlled-release portion contains 25% of doxycycline.

3. The pharmaceutical composition according to claim 1, wherein the immediate-release portion contains 30 mg of doxycycline and the controlled-release portion contains 10 mg of doxycycline.

4. The pharmaceutical composition according to claim 1, wherein the immediate-release portion contains 65% of doxycycline and the controlled-release portion contains 35% of doxycycline.

5. The pharmaceutical composition according to claim 1, wherein the immediate-release portion contains 26 mg of doxycycline and the controlled-release portion contains 14 mg of doxycycline.

6. The pharmaceutical composition according to claim 1, wherein the immediate-release portion contains 60% of doxycycline and the controlled-release portion contains 40% of doxycycline.

7. The pharmaceutical composition according to claim 1, wherein the immediate-release portion contains 24 mg of doxycycline and the controlled-release portion contains 16 mg of doxycycline.

8. The pharmaceutical composition according to claim 1, wherein the controlled-release polymer is a cellulose polymer.

9. The pharmaceutical composition according to claim 1, wherein the one or more pharmaceutically acceptable excipients are selected from the group comprising binders, diluents, disintegrants, lubricants/glidants/antiadherants, plasticizers, or mixtures thereof.

10. The pharmaceutical composition according to claim 1, wherein the pharmaceutical composition is in the form of tablet.

11. A process for the preparation of a pharmaceutical composition comprising (i) 50% to 99% of doxycycline and one or more pharmaceutically acceptable excipients as an immediate-release portion; and (ii) 1% to 50% of doxycycline, a controlled-release polymer, and one or more pharmaceutically acceptable excipients as a controlled-release portion, wherein the pharmaceutical composition provides a total daily dosage of 40 mg when administered once daily, and wherein the process comprises:
- a) preparing the immediate-release portion comprising doxycycline and one or more pharmaceutically acceptable excipients;
- b) preparing the controlled-release portion comprising doxycycline, a controlled-release polymer, and one or more pharmaceutically acceptable excipients; and
- c) processing the immediate-release portion and the controlled-release portion to form the pharmaceutical composition.

12. A method of treating rosacea by administering to a patient in need thereof a pharmaceutical composition comprising (i) 50% to 99% of doxycycline and one or more pharmaceutically acceptable excipients as an immediate-release portion; and (ii) 1% to 50% of doxycycline, a controlled-release polymer, and one or more pharmaceutically acceptable excipients as a controlled-release portion, wherein the pharmaceutical composition provides a total daily dosage of 40 mg when administered once daily.

\* \* \* \* \*